(12) United States Patent
Kim et al.

(10) Patent No.: US 7,742,616 B2
(45) Date of Patent: Jun. 22, 2010

(54) ELECTROMAGNETIC ACOUSTIC TRANSDUCER FOR GENERATING AND MEASURING BENDING VIBRATION IN ROD MEMBER USING ANTI-SYMMETRIC MAGNETIC FIELD STRUCTURE

(75) Inventors: Yoon Young Kim, Seoul (KR); Soon Woo Han, Seoul (KR)

(73) Assignee: Seoul National University Industry Foundation, Seoul (KR)

( * ) Notice: Subject to any disclaimer, the term of this patent is extended or adjusted under 35 U.S.C. 154(b) by 1183 days.

(21) Appl. No.: 11/287,370

(22) Filed: Nov. 28, 2005

(65) Prior Publication Data
US 2006/0210100 A1    Sep. 21, 2006

(30) Foreign Application Priority Data
Mar. 3, 2005    (KR) .................. 10-2005-0017668

(51) Int. Cl.
*H04R 25/00*    (2006.01)
(52) U.S. Cl. .................. 381/396; 381/400; 381/412
(58) Field of Classification Search .................. 381/150, 381/396, 400, 412, 420, 421
See application file for complete search history.

(56) References Cited
FOREIGN PATENT DOCUMENTS

| | | |
|---|---|---|
| JP | 163746 | 4/1944 |
| JP | 169326 | 1/1945 |
| JP | 53157850 | 12/1978 |
| JP | 55111304 | 8/1980 |
| JP | 562230 | 1/1981 |
| JP | 59009528 | 1/1984 |
| JP | 59228162 | 12/1984 |
| JP | 60105960 | 6/1985 |
| JP | 63109338 | 5/1988 |
| JP | 64086030 | 3/1989 |
| KR | 57-41373 | 8/1980 |

OTHER PUBLICATIONS

Gori, et al., "Guided waves by EMAT transducers for rapid defect location on heat exchanger and boiler tubes", Ultrasonics, 1996, pp. 311-314, vol. 34.
Hirao, et al., "An SH-wave EMAT technique for gas pipeline inspection" NDT&E International, 1999, pp. 127-132, vol. 32.
Martin, et al., "Flexural plate wave resonator excited with Lorentz forces". Journal of Applied Physics, 1998, pp. 4589-4601, vol. 83(9).
JP Office Action and English translation for JP 2005-375932 dated Nov. 29, 2007, 8 pages.

*Primary Examiner*—Tuan D Nguyen
(74) *Attorney, Agent, or Firm*—Rothwell, Figg, Ernst & Manbeck, PC

(57) ABSTRACT

Provided is an electromagnetic acoustic transducer including a main body formed of a non-metal material and having a hollow portion, a magnetic field generation portion generating two magnetic fields parallel to a lengthwise direction of the rod member and in opposite directions to each other, at both sides of the rod member that is inserted in the hollow portion of the main body, and a coil wound around an outer circumferential surface of the main body.

4 Claims, 8 Drawing Sheets

ELECTROMAGNETIC ACOUSTIC TRANSDUCER FOR GENERATING AND MEASURING BENDING VIBRATION IN ROD MEMBER USING ANTI-SYMMETRIC MAGNETIC FIELD STRUCTURE

CROSS-REFERENCE TO RELATED PATENT APPLICATIONS

This application claims the benefit of Korean Patent Application No. 10-2005-0017668, filed on Mar. 3, 2005, in the Korean Intellectual Property Office, the disclosure of which is incorporated herein in its entirety by reference.

BACKGROUND OF THE INVENTION

1. Field of the Invention

The present invention relates to an electromagnetic acoustic transducer (EMAT), and more particularly, to an EMAT which can generate and measure a bending vibration in a rod member by generating a magnetic field around the rod member and converting wave energy transferred to the rod member into electric energy or transferring a wave to the rod member by inducing a change in the magnetic field.

2. Description of the Related Art

EMATs refer to devices which can operate as a non-contact sensor and an actuator using Lorentz's force, an electromagnetic induction phenomenon, and an electromagnetic phenomenon such as an eddy current. In particular, since the use of EMATs enables a non-destructive non-contact testing of a material, the applicable fields of the EMATs have gradually increased.

However, the applicable fields of the EMATs have been limited to the measurement of axial shear waves or torsional waves in a rod member and longitudinal waves or transverse waves in a plate member. That is, no EMAT capable of measuring a bending vibration acting on a rod member or generating a bending vibration in the rod member has yet been developed.

SUMMARY OF THE INVENTION

To solve the above and/or other problems, the present invention provides an EMAT which can generates a bending vibration in a rod member or measure a bending vibration acting on the rod member.

According to an aspect of the present invention, an electromagnetic acoustic transducer comprises a main body formed of a non-metal material and having a hollow portion, a magnetic field generation portion generating two magnetic fields parallel to a lengthwise direction of the rod member and in opposite directions to each other, at both sides of the rod member that is inserted in the hollow portion of the main body, and a coil wound around an outer circumferential surface of the main body.

The magnetic field generation portion comprises a first pair of magnets arranged at one side of the main body and separated a predetermined distance from each other; and a second pair of magnets arranged symmetrical to the first pair of magnets with respect to the rod member and generating a magnetic field in a direction opposite to a direction of a magnetic field generated by the first pair of magnets.

The main body comprises a coil portion around which the coil is wound; and first and second rotational portions located at both sides of the coil portion, coupled to the coil portion, and capable of rotating at the same angle with respect to the coil portion.

The magnetic field generation portion is installed at each of the first and second rotational portions.

BRIEF DESCRIPTION OF THE DRAWINGS

The above and other features and advantages of the present invention will become more apparent by describing in detail preferred embodiments thereof with reference to the attached drawings in which.

DETAILED DESCRIPTION OF THE INVENTION

Figure 1:
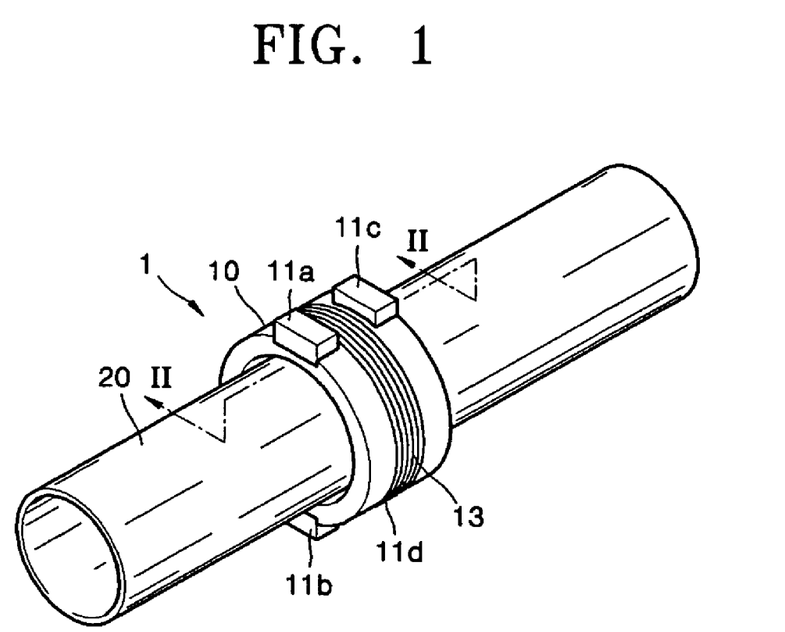
FIG. 1 is a perspective view of an EMAT according to an embodiment of the present invention.
Figure 2:
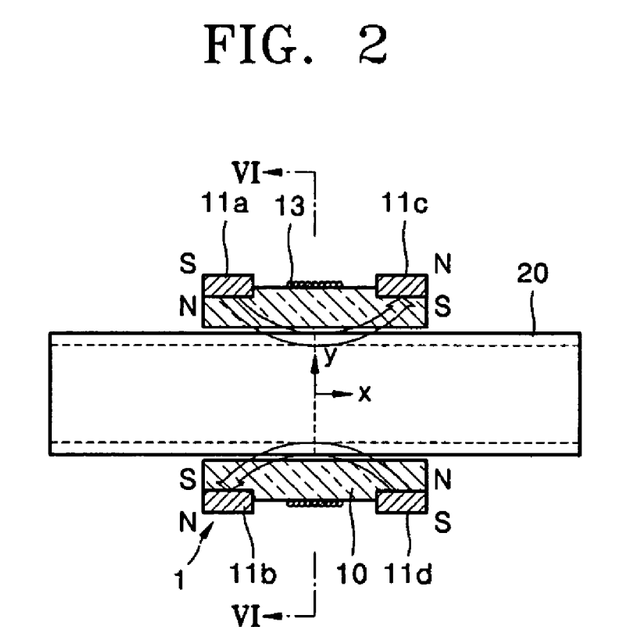
FIG. 2 is a sectional view taken along line II-II of FIG. 1.

Referring to FIG. 1, an electromagnetic acoustic transducer (EMAT) 1 includes a main body 10, magnets 11a, 11b, 11c, and 11d, and a coil 13. The main body 10 is formed of a non-metal material and has a hollow portion in which a rod member 20 such as a pipe or a rotational shaft can be inserted. The magnets 11a, 11b, 11c, and 11d are installed at four positions on the main body 10 and arranged around the outer circumferential surface of the rod member 20 that is inserted in the hollow portion of the main body 10. The magnets 11a, 11b, 11c, and 11d generate magnetic fields in a lengthwise direction of the rod member 20. In detail, as shown in FIG. 2, the magnetic fields generated by the magnets 11a, 11b, 11c, and 11d are generated along the outer circumferential surface of the rod member 20 parallel to the lengthwise direction of the rod member 20. In particular, the magnetic field at one side generated by the magnets 11a and 11c has an opposite direction to the magnetic field at the other side generated by the magnets 11b and 11d that are located at positions symmetrical to the magnets 11a and 11c, respectively. That is, the magnetic fields are anti-symmetric along the circumferential direction of the rod member 20.

In FIG. 2, the magnets 11a and 11b are installed such that the N poles thereof face downward while the magnets 11c and 11d are installed such that the N poles thereof face upward. The number and arrangement of the magnets used in the EMAT according to the present embodiment are not limited to those shown in FIGS. 1 and 2. Any number and arrangement of magnets can be adopted which can generate magnetic fields parallel to the lengthwise direction of the rod member and in opposite directions to each other at the upper and lower sides of the rod member 20. The coil 13 is wound around the outer circumferential surface of the main body 10 at the center portion thereof to avoid the positions where the magnets are installed.

Figure 3:
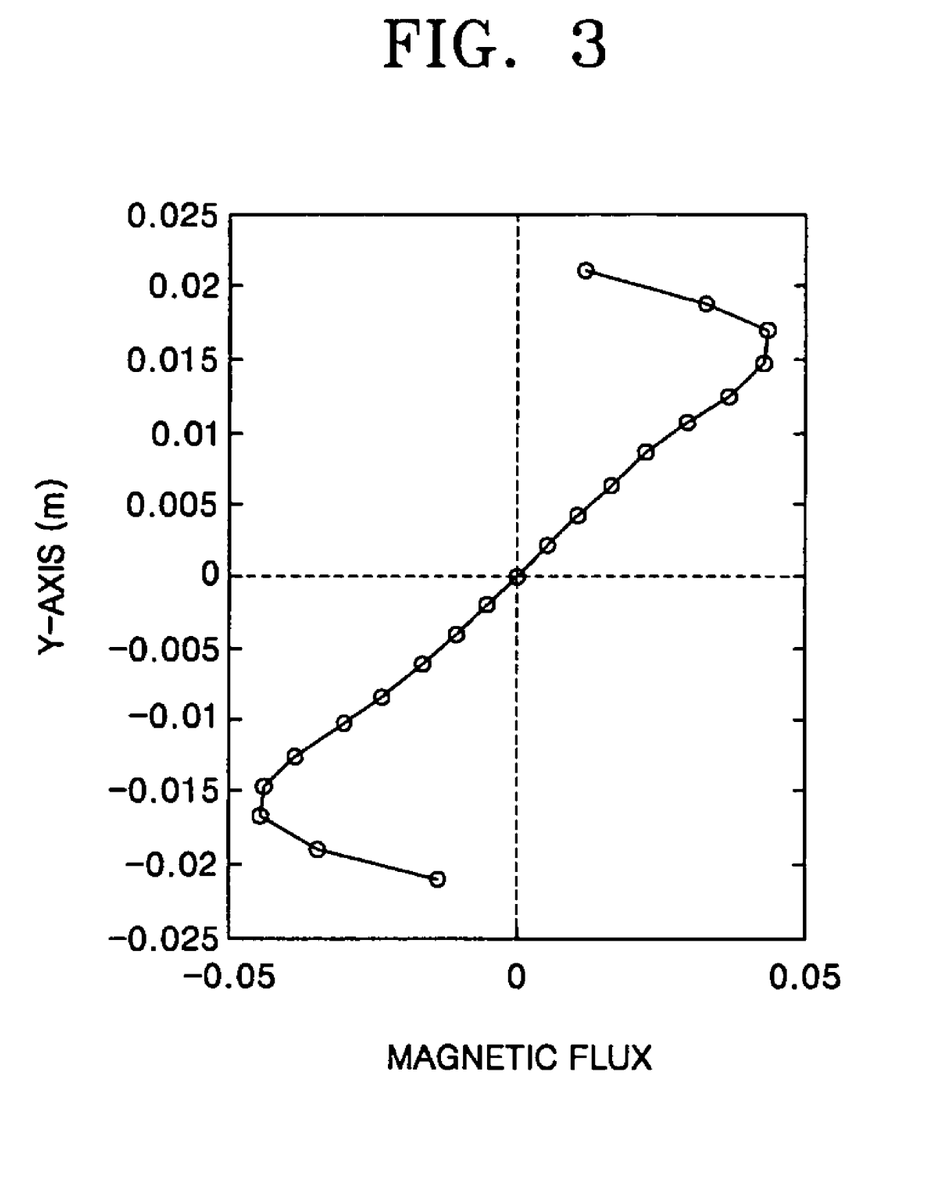
FIG. 3 is a graph showing the magnetic flux density distributed along the y axis in FIG. 2.

FIG. 3 is a graph showing the magnetic flux density distributed along the y axis in FIG. 2. Referring to FIG. 3, the magnetic flux at the center of the rod member 20 along the y axis is 0 as the magnetic fields generated by the magnets 11a and 11c, and 11b and 11d, at the upper and lower sides of the rod member 20 offset each other. The magnetic fluxes at the upper and lower sides in the graph are anti-symmetric with respect to the vertical axis.

Figure 4:
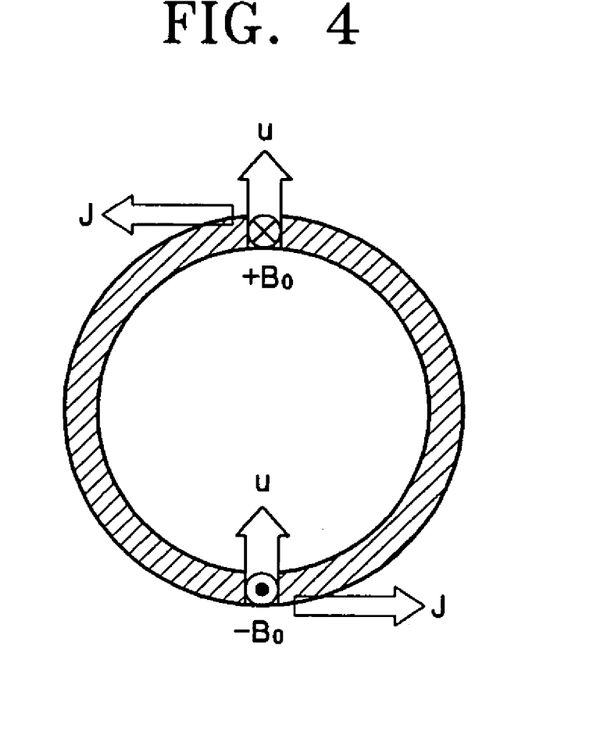
FIG. 4 is a sectional view taken along line IV-IV of FIG. 2.

FIG. 4 is a sectional view taken along line IV-IV of FIG. 2, showing the principle of generating and measuring of a bending vibration. In the description of the principle of the present invention with reference to FIG. 4, the rod member 20 is formed of a conductive material such as a metal. Nevertheless, the present invention is not limited to the above description and a method of applying the present invention to a rod member formed of a non-conductive material will be described later.

As shown in FIG. 4, when a magnetic field is generated at the upper side of the rod member 20 in a direction going into the page and at the lower side in a direction going out of the page, a bending vibration can be generated in the other portion of the rod member. The bending vibration is generated in a direction in which the rod member 20 is bent and transferred in the lengthwise direction of the rod member. At a certain point, both upper and lower sides of the rod member 20 are simultaneously displaced upward as shown in FIG. 4. At this time, an eddy current is generated at the upper and lower sides of the rod member 20 in a direction perpendicular to each of directions of the magnetic field and the displacement. As the eddy current in a counterclockwise direction is generated at the same time when the upward displacement occurs, the eddy current circulates along the outer circumferential direction of the rod member 20. The magnitude of the eddy current can be represented as in Equation 1.

$$J = \frac{\partial u}{\partial t} \times B \quad \text{[Equation 1]}$$

Here, "J" denotes a current, "u" denote an amplitude, "t" denotes time, and "B" denotes the density of the magnetic flux. Since the eddy current causes an electromotive force in the coil 13, the bending vibration can be obtained by measuring the electromotive force generated in the coil 13.

Figure 5:
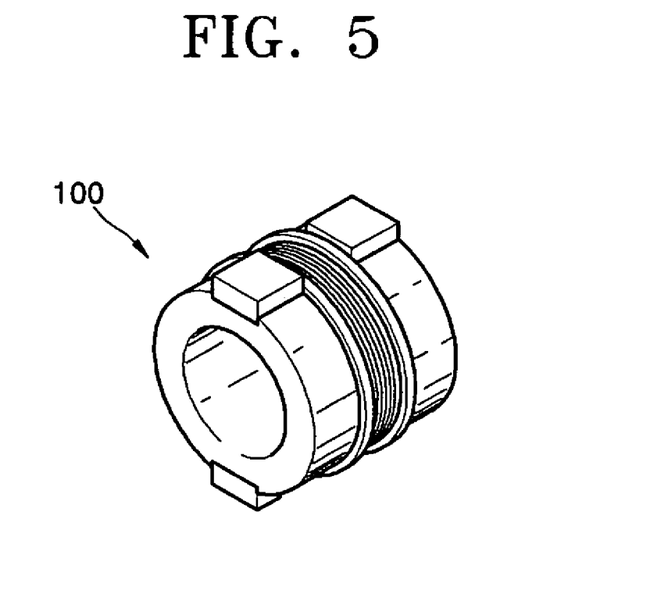
FIG. 5 is a perspective view of an EMAT according to another embodiment of the present invention.
Figure 6:
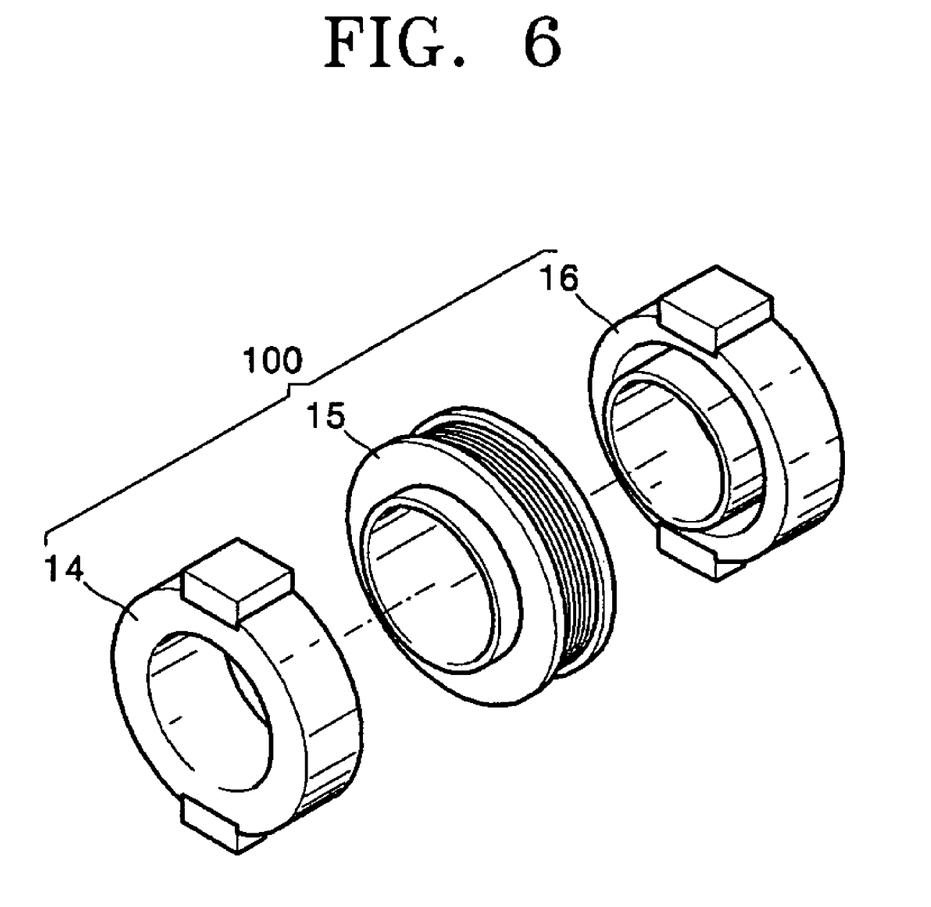
FIG. 6 is an exploded perspective view of the EMAT of FIG. 5.

FIG. 5 is a perspective view of an EMAT according to another embodiment of the present invention. FIG. 6 is an exploded perspective view of the EMAT of FIG. 5. Referring to FIGS. 5 and 6, in the EMAT according to present embodiment, a main body 100 includes a coil portion 15, a first rotational portion 14, and a second rotational portion 16. The first and second rotational portions 14 and 16 are installed to be capable of rotating at the same angle with respect to the coil portion 15. That is, the first and second rotational portions 14 and 16 are connected in a hollow portion of the coil portion 15. Magnets for generating magnetic fields are installed on the first and second rotational portions 14 and 16.

When the above EMAT is used, of the bending vibrations in the rod member 20, only a bending vibration passing the upper and lower sides of the rod member 20 as shown in FIG. 4 can be measured. However, when the magnetic field generation portion is rotatably provided as shown in FIGS. 5 and 6, since the magnetic field generation position can be arbitrarily changed along the circumference of the rod member 20, the bending vibrations in all directions can be measured.

In the meantime, a bending vibration can be generated in the rod member by changing a current flowing in the coil in an EMAT having the same structures as described in the above embodiments. That is, by changing the current flowing in the coil, the eddy current is generated on the surface of the rod member in a direction to disturb the change of the current. The rod member receives the Lorentz's force by the eddy current and the magnetic field generated by the magnets. Accordingly, a bending vibration is generated in the rod member.

The following system is constructed when the bending vibration applied to the rod member 20 is measured or the bending vibration is generated in the rod member 20 using the EMAT 1 according to the present invention.

Figure 7:
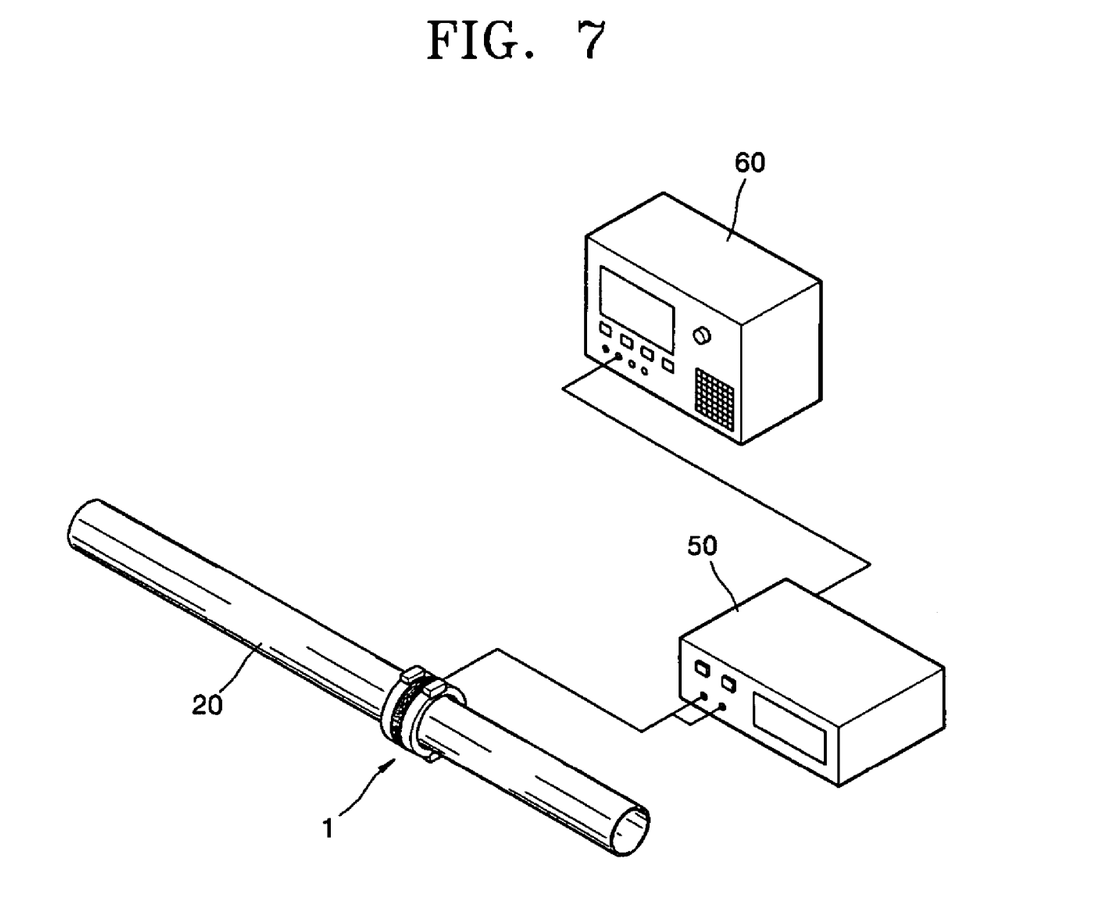
FIG. 7 is a reference view showing the structure of a system for generating and measuring a bending vibration, the system including an EMAT according to the present invention.

FIG. 7 is a reference view showing the structure of a system for generating and measuring a bending vibration, the system including the EMAT according to the present invention. Referring to FIG. 7, a system for generating a bending vibration includes an EMAT 1 according to the present invention, an amplifier 50 connected to a coil of the EMAT 1, and an oscilloscope 60 processing an analog signal passing through the amplifier 50. Thus, a bending vibration can be generated or measured.

A Modal testing can be performed with respect to a rod member using the EMAT according to the present invention. The result of performing a Modal testing with respect to a rod member by measuring a bending vibration in the rod member using the EMAT according to the present invention is described below.

Figure 8:
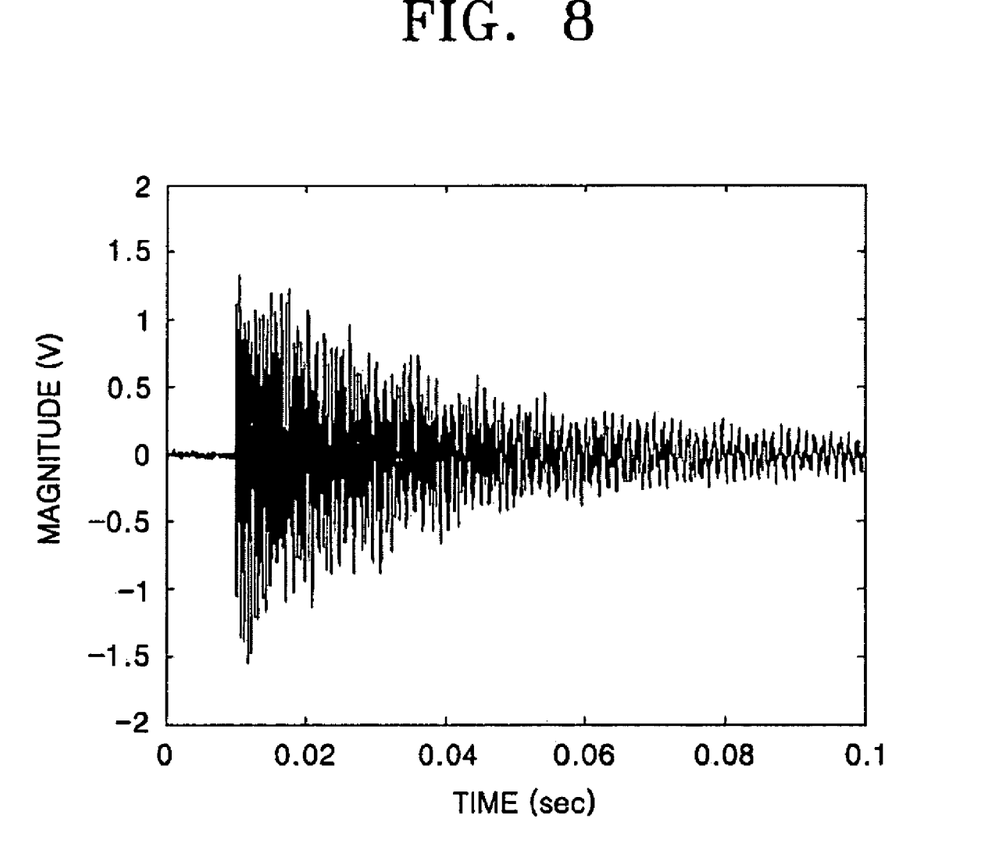
FIG. 8 is a graph showing an example of bending vibration measured when a Modal testing is performed using the EMAT according to the present invention.
Figure 9:
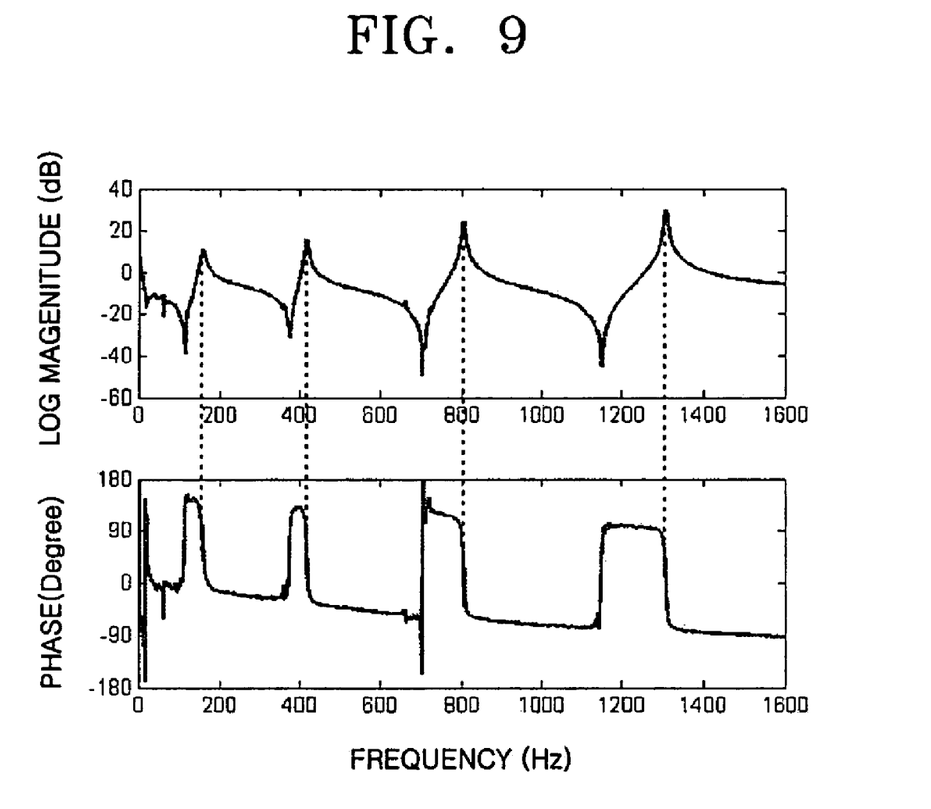
FIG. 9 shows Bode plots of a frequency response function which can determine a natural frequency as a result of performing a Modal testing using the EMAT according to the present invention.
Figure 10:
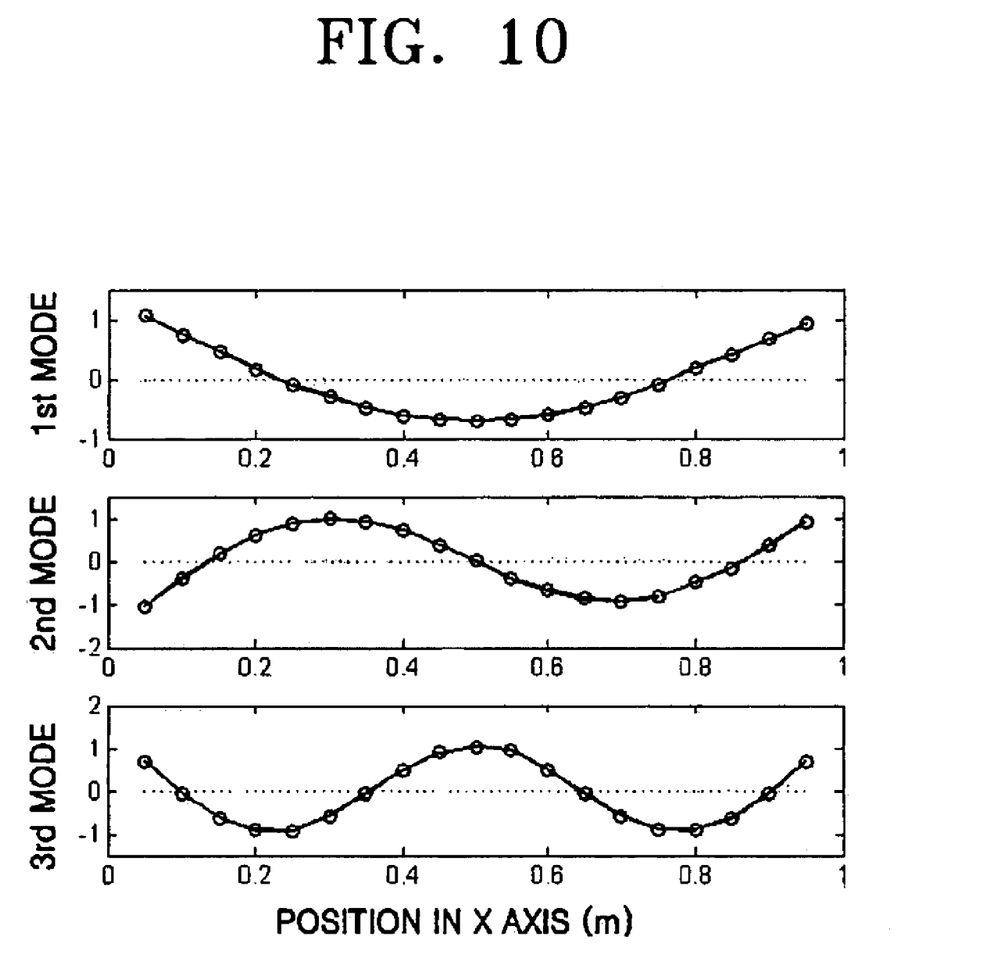
FIG. 10 shows mode shapes as a result of performing a Modal testing using the EMAT according to the present invention.

FIGS. 8 through 10 show the results of a Modal testing with respect to a pipe using the EMAT according to the present invention. In the testing, an aluminum pipe having an outer diameter of 25 mm, a thickness of 1.5 mm, and a length of 1 m was used. A bending vibration signal as shown in FIG. 8 can be measured by using the EMAT according to the present invention. Also, when the EMAT according to the present invention is used, a frequency response function as shown in FIG. 9 and mode shapes regarding a bending vibration as shown in FIG. 10 can be obtained.

In FIG. 9, a frequency response function is shown in Bode plots of a magnitude-phase pattern because the position of the natural frequency and the size of a mode vector for each natural frequency can be easily obtained. The frequency response function of an undamped single degree of freedom system can be represented as in Equation 2.

$$H = \frac{1/m}{\omega_n^2 - \omega^2} \quad \text{[Equation 2]}$$

As the frequency "$\omega$" approaches the natural frequency "$\omega_n$", the denominator of the frequency response function becomes close to 0 so that the magnitude of the function is maximized in the vicinity of the natural frequency. At this time, the real number portion of the frequency response function approaches 0, the imaginary number portion becomes maximum, and the phase is defined to be $\tan^{-1}$ (imaginary number portion/real number portion) so that the phase has a value of 90 degrees in the vicinity of the natural frequency. The peaks in the frequency response function denote the natural frequency of the rod member not only because the magnitude of the frequency response function is maximum, but because the phase is calculated to be 90 degrees on the Bode plot. When a mode vector value of a particular natural frequency is dominant, if the frequency response function is drawn in linear scale, it is liable to miss other natural frequencies. Therefore, the frequency response function is desirable to be drawn in log scale. That is, in FIG. 9, the natural frequency can be obtained by reading a frequency of a portion connected by a dotted line.

In FIG. 10, circles indicate experimental values of a mode shape with respect to a bending vibration and a solid line indicates theoretical values. The natural frequency and mode shapes of the rod member (aluminum pipe) subject to measurement are obtained from the result shown in FIGS. 9 and 10. The natural frequency and mode shapes of the rod member obtained as above are reflected to design of a machine including the rod member subject to measurement. That is, the results of Modal testing is used as a guideline of design such that the frequency of the vibration applied to the rod member in an actual operation state is different from the natural frequency measured through the Modal testing. Therefore, the rod member can be prevented from being damaged by the vibration or resonance of the vibration considering the natural frequency and the mode shapes.

Although the above-described embodiments mainly discussed the rod member having a pipe shape and a hollow portion, the present invention can be also applied to all rod members including a rotational shaft having a circular section.

Also, it is noted that the EMAT according to the present invention is not applied only to the rod member 20 having an electric conductivity. That is, the EMAT can be applied to a rod member formed of a non-metal material by enclosing the outer circumference of the rod member that is not conductive with a thin film member having electric conductivity. In this case, the conductive thin film member is attached to the outer circumferential surface of the non-conductive rod member. For example, when a non-metal pipe such as a PVC pipe is enclosed with a copper foil tape, an eddy current in a circumferential direction is generated in the copper foil tape due to the bending vibration and an anti-symmetric magnetic field along the non-metal pipe so that the bending vibration of the non-metal pipe can be measured.

As described above, in the EMAT according to the present invention, the bending vibration transferred to the rod member can be measured using the EMAT in which an anti-symmetric magnetic field is generated. Also, the bending vibration can be generated in the rod member using the EMAT having the same structure.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. An electromagnetic acoustic transducer which can generate and measure a bending vibration in a rod member comprising:
   a main body formed of a non-metal material and having a hollow portion;
   a magnetic field generation portion generating two magnetic fields parallel to a lengthwise direction of the rod member and in opposite directions to each other, at both sides of the rod member that is inserted in the hollow portion of the main body; and
   a coil wound around an outer circumferential surface of the main body.

2. The electromagnetic acoustic transducer as claimed in claim 1, wherein the magnetic field generation portion comprises:
   a first pair of magnets arranged at one side of the main body and separated a predetermined distance from each other; and
   a second pair of magnets arranged symmetrical to the first pair of magnets with respect to the rod member and generating a magnetic field in a direction opposite to a direction of a magnetic field generated by the first pair of magnets.

3. The electromagnetic acoustic transducer as claimed in claim 1, wherein the main body comprises:
   a coil portion around which the coil is wound; and
   first and second rotational portions located at both sides of the coil portion, coupled to the coil portion, and capable of rotating at the same angle with respect to the coil portion.

4. The electromagnetic acoustic transducer as claimed in claim 3, wherein the magnetic field generation portion is installed at each of the first and second rotational portions.

* * * * *